(12) United States Patent
Suh et al.

(10) Patent No.: US 9,579,136 B2
(45) Date of Patent: Feb. 28, 2017

(54) DISTRACTION SCREW

(71) Applicants: Sean Suh, Plymouth Meeting, PA (US); Michal Zentko, Florham Park, NJ (US); Andrew Iott, Villanova, PA (US); Kurt Faulhaber, Plymouth Meeting, PA (US); David C Paul, Phoenixville, PA (US)

(72) Inventors: Sean Suh, Plymouth Meeting, PA (US); Michal Zentko, Florham Park, NJ (US); Andrew Iott, Villanova, PA (US); Kurt Faulhaber, Plymouth Meeting, PA (US); David C Paul, Phoenixville, PA (US)

(73) Assignee: Globus Medical, Inc., Audubon, PA (US)

(*) Notice: Subject to any disclaimer, the term of this patent is extended or adjusted under 35 U.S.C. 154(b) by 339 days.

(21) Appl. No.: 14/186,821

(22) Filed: Feb. 21, 2014

(65) Prior Publication Data
US 2015/0238230 A1 Aug. 27, 2015
US 2016/0374726 A9 Dec. 29, 2016

Related U.S. Application Data

(63) Continuation of application No. 13/106,583, filed on May 12, 2011, now Pat. No. 8,690,917.

(60) Provisional application No. 61/334,004, filed on May 12, 2010.

(51) Int. Cl.
*A61B 17/88* (2006.01)
*A61B 17/84* (2006.01)
*A61B 17/56* (2006.01)
*A61B 17/86* (2006.01)
*A61B 17/70* (2006.01)

(52) U.S. Cl.
CPC .............. *A61B 17/88* (2013.01); *A61B 17/56* (2013.01); *A61B 17/70* (2013.01); *A61B 17/84* (2013.01); *A61B 17/844* (2013.01); *A61B 17/86* (2013.01); *A61B 17/863* (2013.01); *A61B 17/864* (2013.01); *A61B 17/8685* (2013.01); *A61B 2017/564* (2013.01)

(58) Field of Classification Search
CPC ... A61B 17/56; A61B 2017/564; A61B 17/70; A61B 17/84; A61B 17/844; A61B 17/86; A61B 17/863; A61B 17/864; A61B 17/8685; A61B 17/88
See application file for complete search history.

(56) References Cited

U.S. PATENT DOCUMENTS

2007/0168036 A1* 7/2007 Ainsworth ........... A61B 17/025
  623/17.13
2011/0282387 A1* 11/2011 Suh ........................ A61B 17/70
  606/246

FOREIGN PATENT DOCUMENTS

IL WO 2009113077 A2 * 9/2009 ........... A61F 2/4455

* cited by examiner

*Primary Examiner* — Larry E Waggle, Jr.

(57) ABSTRACT

A distraction screw includes a proximal portion secured to a first vertebra, a distal portion secured to a second vertebra and an intermediate portion. The intermediate portion is coupled to the proximal and distal portions and is positioned in an intervertebral space. The intermediate portion is configured and adapted to enable distraction of the first vertebra relative to the second vertebra.

20 Claims, 7 Drawing Sheets

DISTRACTION SCREW

CROSS REFERENCE TO RELATED APPLICATIONS

This application is a continuation of U.S. application Ser. No. 13/106,583, filed May 12, 2011, which claims priority to provisional application Ser. No. 61/334,004 filed on May 12, 2010, all of which are incorporated herein by reference in their entirety.

FIELD OF THE INVENTION

The present disclosure generally relates to a fixation device for positioning and immobilizing at least two adjacent vertebra.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses. Typically, weaknesses in the spine are corrected by using devises that fuse one or more vertebrae together. There is a need for variations of a new screw that can be used to distract vertebrae and restore as well as maintain disc height while keeping the lumber vertebrae in its natural alignment through a combination of rigid/semi-rigid or pivoting screw segments.

SUMMARY OF THE INVENTION

The present invention provides a distraction screw which includes a proximal portion secured to a first vertebra, a distal portion secured to a second vertebra and an intermediate portion. The intermediate portion is coupled to the proximal and distal portions and is positioned in an intervertebral space between two adjacent vertebrae. The intermediate portion is configured and adapted to enable distraction of the first vertebra relative to the second vertebra.

BRIEF DESCRIPTION OF THE DRAWINGS

The invention will be more fully understood from the following detailed description taken in conjunction with the accompanying drawings, in which:

FIGS. 2-4 illustrate the method of implanting the distracting screw according to the preferred embodiment.

FIGS. 5-10 illustrate another embodiment of a distraction screw and a method of using the distraction screw 32 according to the present invention.

DETAILED DESCRIPTION OF THE PREFERRED EMBODIMENTS

While it is apparent that the invention disclosed herein is well calculated to fulfill the objects stated above, it will be appreciated that numerous modifications and embodiments may be devised by those skilled in the art.

Figure 1:
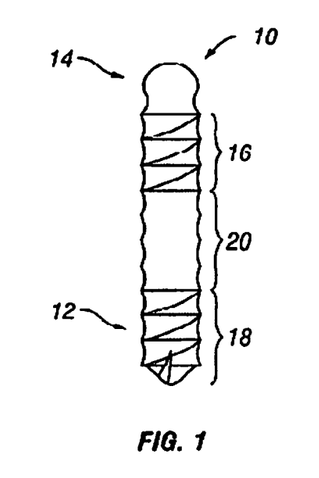
FIGS. 1-4 illustrate an axially distracting screw and a method for laterally positioning the screw within the spine.

FIGS. 1-4 illustrate an axially distracting screw and a method for laterally positioning the screw within the spine. FIG. 1 shows a distracting screw 10 having a shank portion 12 and a head portion 14. The shank portion 12 includes a first semi-rigid portion 16 and a second semi-rigid portion 18. The shank portion 12 is also configured with a rigid portion 20 positioned between the first and second semi-rigid portions 16 and 18. The first semi-rigid portion 16 and the second semi-rigid portion 18 are provided with threads that enable bone purchase and allow for the screw to advance through the bone in a curved trajectory. When the distraction screw 10 is threaded into its final position, the rigid portion 20 is positioned to be between the two endplates of the adjacent vertebrae resisting shear forces. The distraction screw 10 also allows for axial distraction of two or more vertebrae without lateral translation of the vertebral body.

Figure 2:
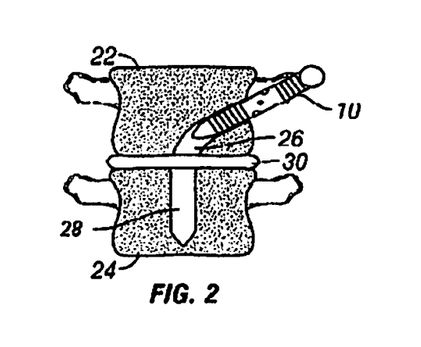
Figure 3:
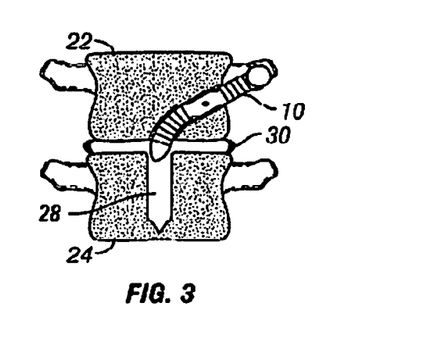
Figure 4:
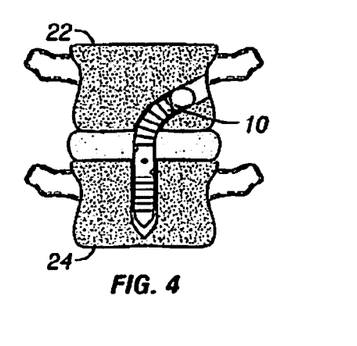

FIGS. 2-4 also illustrate the method of implanting the distracting screw according to the preferred embodiment. Initially, a curved pilot hole 26 is created though the first vertebrae 22 and a straight pilot hole 28 is created in the second vertebrae 24. The curved pilot hole 26 and the straight pilot hole 28 are continuous through the disc space 30. After, the pilot holes 26 and 28 are created, a distraction screw 10 is threaded through the hole 26 of the first vertebrae 22 and then through the hole 28 in the second vertebrae 24. In some embodiments, the distraction screw 10 is configured to allow for bone growth material to be inserted into the disc space 30. In another embodiment, the distraction screw 10 may be provided with a membrane attached to the screw 10 that will contain cement and/or other biological compatible material for delivering to the proper location within the spine. For instance, pain medication can be inserted through the screw to alleviate any pain generated in the vertebral body or the disc space.

Figure 5:
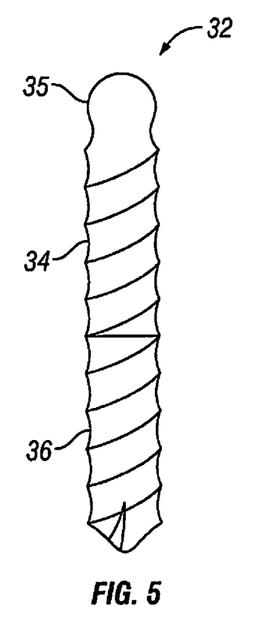
Figure 6:
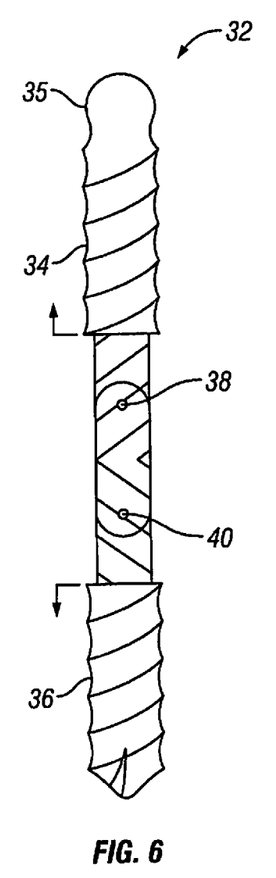

FIGS. 5-10 illustrate another embodiment of a distraction screw 32 and a method of using the distraction screw 32 according to the present invention. Specifically, FIGS. 5 and 6 illustrate the distraction screw 32 comprised of two bone screws 34 and 36 that are coupled together through an inner threaded cannulated portion that links the two bone screws together. The proximal bone screw 34 is configured with screw head 35 which has features that enable it to mate with a driver. When the driver is actuated, the distraction screw 32 is configured to advance the distal bone screw 36. The proximal bone screw 34 and the distal bone screw 36 are configured with threads for purchase with bone. The cannulated portion utilizes a combination of left and right hand threads that allow for translation of the distal and proximal screws 34 and 36. As the actuator is rotated, it exposes the pivot points 38 and 40, allowing the proximal and distal bone screws 34 and 36 to rotate around each of the respective pivot points 38 and 40.

Figure 7:
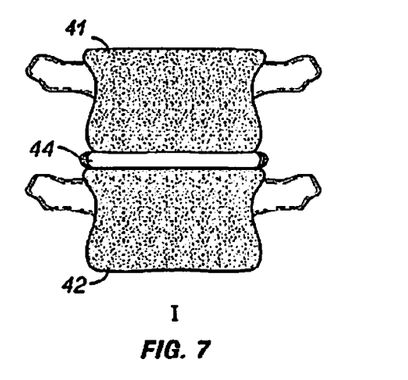
FIGS. 7-10 illustrate the method of positioning the implant according to the present invention within the spinal elements of the body.
Figure 8:
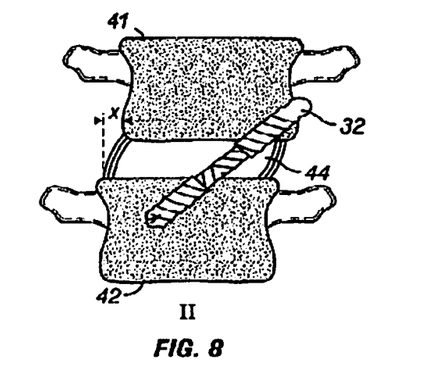
Figure 9:
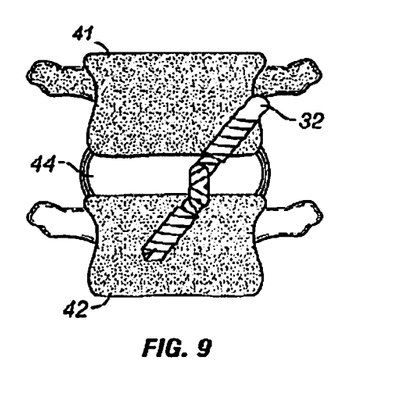
Figure 10:
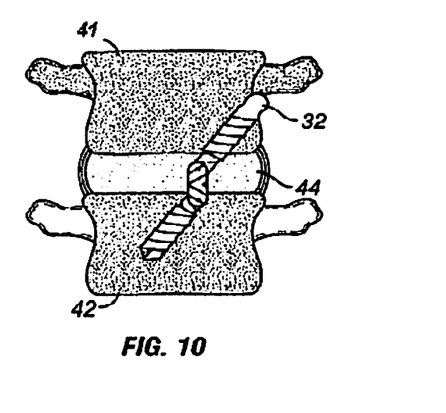

FIGS. 7-10 illustrate the method of positioning the implant according to the present invention within the spinal elements of the body. FIG. 7 shows adjacent vertebrae 41, 42 and intervertebral disc 44. FIGS. 8-10 illustrate the implementation of the distraction screw 32 according to the present invention. The distraction screw 32 is inserted at an oblique angle into the first vertebra 41 through the intervertebral disc 44 and through a portion of the second vertebra 42. As the distraction screw 32 is actuated by a driver, the distal screw 36 is inserted into the second vertebra 42 and the proximal screw 34 is retained within the first vertebra 41. The middle portion of the distraction screw 32 is then positioned within the intervertebral disc space 44. Once the distraction screw is initially positioned, the distraction screw 32 is rotated along the pivot points 38 and 40 to enable distraction between the two adjacent vertebras 41 and 42. More specifically, the cannulated linkage is rotated allowing the proximal and distal screws to separate. As the linkage is further rotated to restore the disc height due to the degenerated disc, the pivot points 38 and 40 are exposed and the supporting musculature and the ligaments help in repositioning the vertebrae. Once the adjacent vertebrae are in the optimal position, bone graft or other biomaterial may be positioned in the intervertebral disc space 44 allowing fusion to occur. Bone cement may also be inserted into the vertebral body or disc space 44 to fuse the adjacent vertebrae. The distraction screw 32 may also be provided with a membrane that encloses the screw 32 which may contain bone cement.

Figure 11:
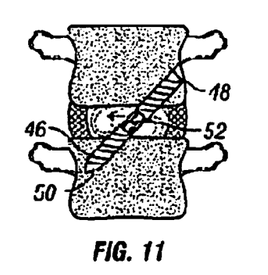
FIGS. 11 and 12 illustrate yet another embodiment of a distraction screw according to the present invention.
Figure 12:
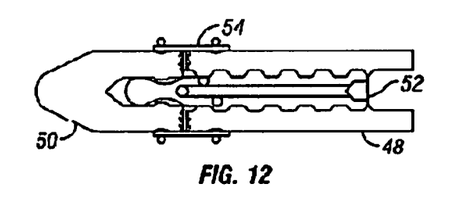

FIGS. 11 and 12 illustrate yet another embodiment of the present invention. Specifically, this embodiment of a distraction screw 46 is comprised of proximal and distal bone screws 48 and 50 and an inner threaded cannulated actuator 52. The proximal bone screw 48 has features that mate with a driver and has features that help to advance the distal bone screw 50. The cannulated actuator 52 allows for the translation of the distal bone screw 50 with respect to the proximal bone screw 48 and is captured within the proximal screw 48 by an interference fit. It contains several outlets for dispensing cement into a compliant membrane 54. The compliant membrane 54 is attached to the screw mechanically or chemically.

Figure 13:
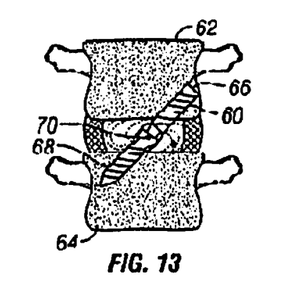
FIGS. 13-15 illustrate yet another embodiment of a distraction mechanism according to the present invention.
Figure 14:
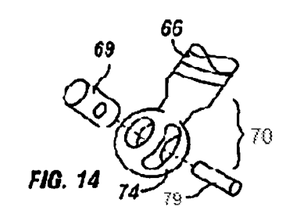
Figure 15:
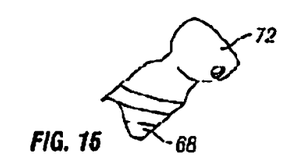

FIGS. 13-15 illustrate yet another embodiment of the present invention. In this particular embodiment, an articulating bone screw 60 that distracts the vertebrae and allows the two adjacent vertebral bodies 62 and 64 to move relative to one another is provided. The articulating bone screw 60 is provided with a proximal end 66, a distal end 68, and a connecting assembly 70 comprising the receiving portion 72 in a portion of the distal end 68 of the articulating bone screw, a connecting portion 74 configured in a portion of the proximal end 66 of the articulating bone screw, a swivel pin 69 and a pin 79. The receiving portion 72 of the distal end 68 is configured and adapted to mate with the connecting portion of the proximal end 66 of the articulating bone screw to create a swivel joint that is secured using swivel pin 69 and pin 79. The swivel pin 69 and pin 79 are configured to couple and allow the distal end 68 to move relative to the proximal end 66 of the articulating bone screw 60.

Figure 16:
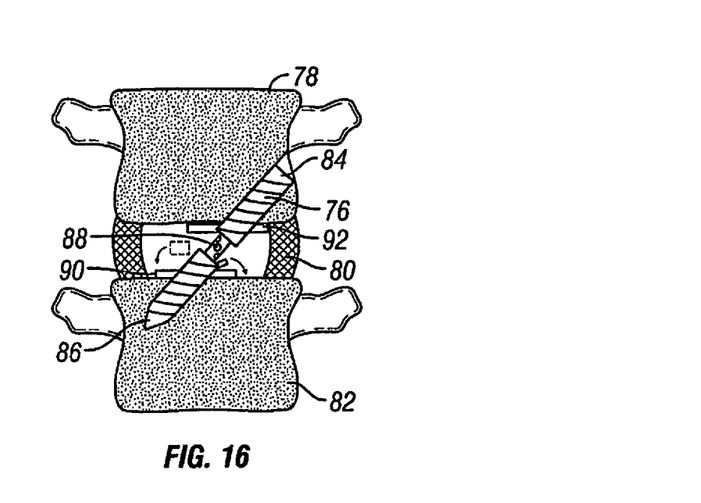
FIG. 16 illustrates another embodiment of a distraction screw according to the present invention.

FIG. 16 illustrates another embodiment of a distraction screw 76 according to the present invention. In this embodiment, the distraction screw 76 is inserted at an oblique angle through a first vertebra 78, the intervertebral disc space 80, and a second adjacent vertebra 82. The distraction screw 76 is configured with a proximal portion 84 and a distal portion 86 with a interior portion 88 that couples the proximal portion 84 and the distal portion 86 together. The interior portion 88 comprises a cannulated actuator and deployable wings 90 and 92. The deployable wings 90 and 92 once deployed distribute the axial loads directed on the bone threads provided on the proximal 84 and distal portions 86 of the distraction screw 76. The deployable wings 90 and 92 are also configured to mitigate the risk subsidence within the intervertebral disc space. Additionally, the deployable wings 90 and 92 are configured and adapted to engage the upper and lower endplates of the first and second vertebrae 78 and 82. The distraction screw 76 distracts the vertebrae using the cannulated actuator within the interior portion 88 of the distraction screw 76.

Figure 17:
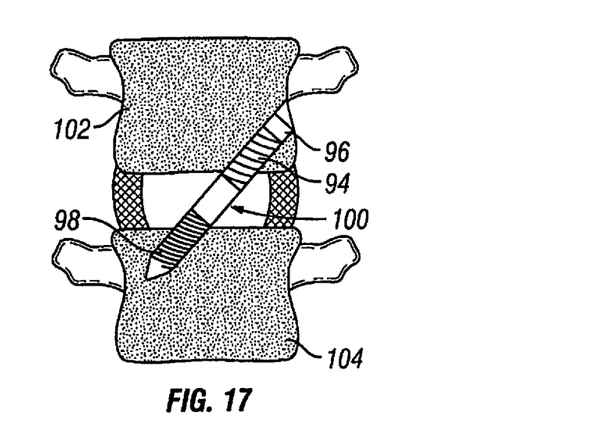
FIG. 17 illustrates yet another embodiment of a distraction screw according to the present invention.

FIG. 17 illustrates yet another embodiment of a distraction screw 94 according to the present invention. In this embodiment, the distraction screw 94 is comprised of a proximal portion 96, a distal portion 98, and middle portion 100 connecting the proximal portion 96 to the distal portion 98. When inserted, the proximal portion 96 of the distraction screw 94 is stabilized within the first vertebra 102 and the distal portion 98 is stabilized within a second vertebra 104. It should be noted that both the proximal and distal portions 96 and 98 are configured with threads that enable optimal purchase to bone. The middle portion 100 is comprised of a polyurethane material (PCU) that enables movement of the proximal portion 96 relative to the distal portion 98 of the distraction screw 94. The polymer core is positioned between the two bone screws and tensioned with a biocompatible core to act as a dampener and a fulcrum. The polymer core of the distraction screw 94 allows for the distraction of the adjacent vertebrae by enabling the two vertebral bodies 102 and 104 to move with respect to each other while maintaining the disc height of the vertebrae.

Figure 18:
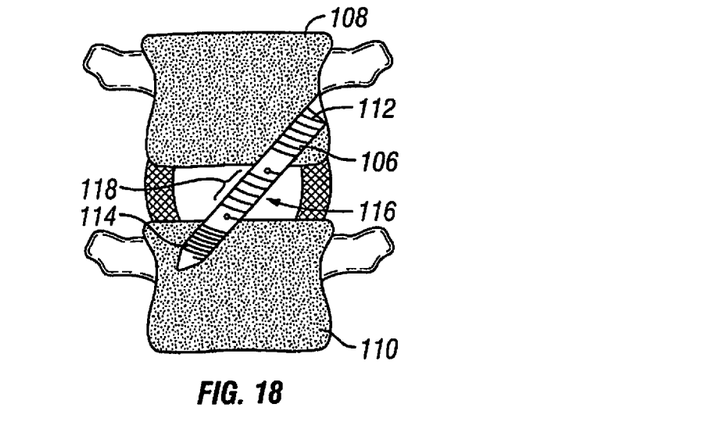
FIG. 18 illustrates yet another embodiment of a distraction screw used in distracting adjacent vertebral segments.

FIG. 18 illustrates yet another embodiment of a distraction screw 106 utilized in distracting adjacent vertebral segments 108 and 110. In this embodiment, the distraction screw 106 is provided with different thread pitch at the proximal 112 and distal 114 ends and a helical cut 116 at the middle section 118. The helical cut 116 extends the length of the middle section 118 and is designed to function as a dampener and a fulcrum. The cuts 116 also provide the distraction screw 106 with a degree of flexibility which allows the distraction of the adjacent vertebrae. The distraction screw 106 as illustrated in FIG. 18 is inserted at an oblique angle and extends from the first vertebra 108 to the second vertebra 110 through the intervertebral space 120.

Figure 19:
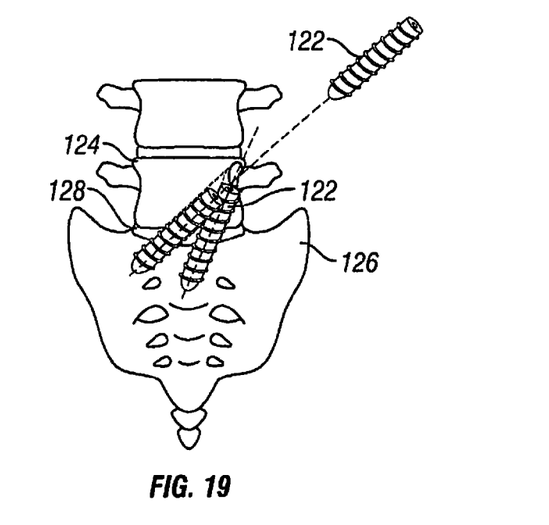
FIG. 19 illustrates yet another embodiment of a fusion system, particularly for fusing the L5-S1 portion of the vertebrae.

FIG. 19 illustrates yet another embodiment of a fusion system, particularly for fusing the L5-S1 portion of the vertebrae. This fusion system enables the fusion of the lumbar portion 124 of the spine with the sacral portion 126 of the spine. In this particular embodiment, multiple screws 122 are inserted into the lumbar portion 124 of the spine and coupled to the sacral portion 126 of the spine through the intervertebral space 128. Specifically, multiple screws 122 are threaded through the lumbar portion 124 through the disc space 128 into the sacral portion 126 of the spine. Each of the screws 122 are inserted through the same opening but take different trajectories through the disc space, as illustrated in FIG. 19.

Figure 20A:
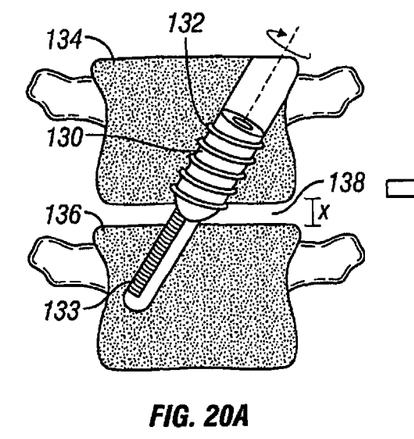
FIGS. 20A and 20B illustrate yet another embodiment of a distraction screw and the method of distraction according to the present invention.
Figure 20B:
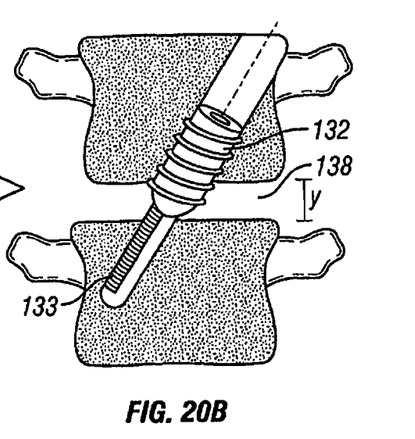

FIGS. 20A and 20B illustrate yet another embodiment of a distraction screw 130 and the method of distraction according to the present invention. In this embodiment, the distraction screw 130 is configured with varying threads in the proximal portion 132 and a shaft on the distal portion 133. By varying the thread design and the shaft size of the distraction screw 130, the implementation of the distraction screw 130 allows the distraction of the first vertebra 134 relative to the second vertebra 136. Specifically, the proximal portion 132 is configured with large threads so that the proximal portion 132 does not extend beyond the intervertebral space 138 and since the proximal portion 132 does not enter the second vertebra 136, as the distraction screw is rotated 130, the first vertebra is distracted relative to the second vertebra, as illustrated in FIG. 20B.

Figure 21A:
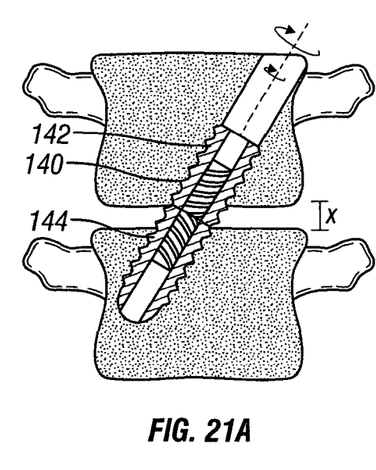
FIGS. 21A and 21B illustrate yet another embodiment of a distraction screw and the method of distraction of adjacent vertebrae according to the present invention.
Figure 21B:
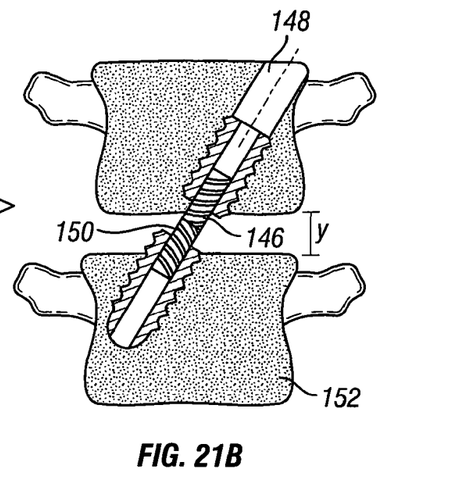

FIGS. 21A and 21B illustrate yet another embodiment of a distraction screw 140 and the method of distraction of adjacent vertebrae according to the present invention. In this embodiment, the distraction screw 140 is configured with a proximal portion 142, a distal portion 144, and an internal threaded shaft 146, the internal threaded shaft 146 is adapted to extend from the proximal portion 142 to the distal portion 144 of the distraction screw. To enable distraction between the adjacent vertebra, the distraction screw 140 is inserted at an oblique angle through the first vertebra 148, the intervertebral disc space 150 and the second vertebra 152. Once the distraction screw 140 is positioned in its optimal position, the outer portion of the screw 140 is secured to remain stationary and the internal threaded shaft 146 is rotated. As the internal threaded shaft 146 is rotated, the proximal portion 142 is disengaged from the distal portion 144, thereby causing distraction between the first vertebra 148 and the second vertebra 152.

Figure 22A:
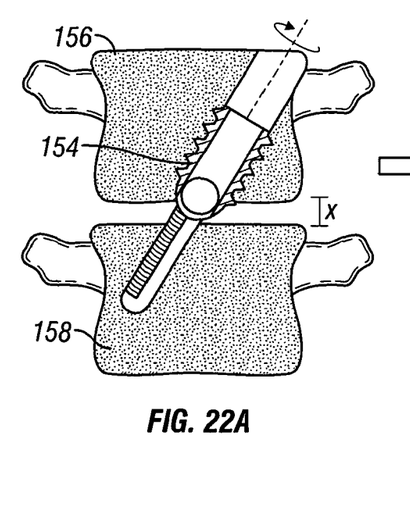
FIGS. 22A and 22B illustrate another embodiment of a distraction mechanism for use in the spine according to the present invention.
Figure 22B:
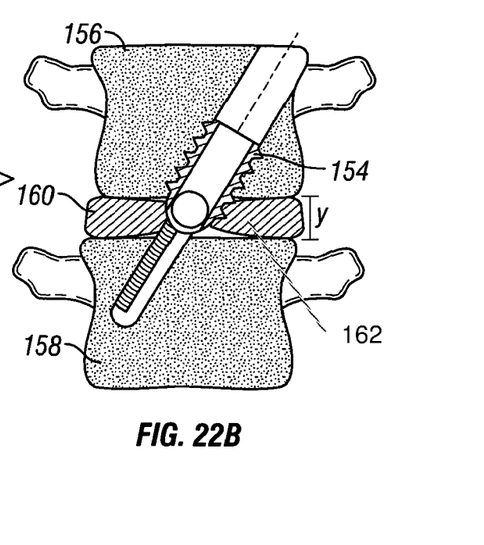

FIGS. 22A and 22B illustrate another embodiment of a distraction mechanism for use in the spine according to the present invention. In this embodiment, a cannulated threaded shaft 154 is provided to engage adjacent vertebrae, 156 and 158. The shaft 154 is provided with at least one aperture for deploying an expandable or deployable spacer 160 within the intervertebral disc space 162. The expandable spacer 160 once deployed enables distraction of the adjacent vertebrae, 156 and 158. It should be noted that varying types of expandable and deployable spacers 160 may be used to achieve this function. It should be further noted that the expandable and deployable spacer may be configured and sized to be in any shape or orientation that would enhance the distraction of the adjacent vertebra. For example, in the preferred embodiment, an inflatable balloon is configured and designed as a spacer which may be deployed through the aperture in the cannulated shaft 154, as illustrated in FIG. 22B.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

What is claimed is:

1. A surgical method comprising:
creating a first hole through a first vertebral body;
creating a second hole through a second vertebral body; and
inserting a distraction screw through the first hole and into the second hole, wherein the distraction screw comprises at least one deployable wing for contacting a lower surface of the first vertebral body.

2. The surgical method of claim 1, wherein the first hole is angled and the second hole is straight.

3. The surgical method of claim 1, wherein the distraction screw comprises a shank portion and a head portion.

4. The surgical method of claim 3, wherein the shank portion comprises a first semi-rigid portion and a second semi-rigid portion separated by a rigid portion.

5. The surgical method of claim 4, wherein the first semi-rigid portion and the second semi-rigid portion are threaded.

6. The surgical method of claim 5, wherein the rigid portion is non-threaded.

7. The surgical method of claim 1, wherein the distraction screw comprises a proximal portion, a middle portion and a distal portion.

8. The surgical method of claim 7, wherein the middle portion comprises at least one pivot point.

9. The surgical method of claim 7, wherein the middle portion comprises a pair of pivot points.

10. The surgical method of claim 7, wherein the middle portion comprises a cannulated linkage.

11. The surgical method of claim 10, wherein the cannulated linkage comprises a pair of pivot points.

12. The surgical method of claim 10, wherein the cannulated linkage helps to restore a damaged disc height.

13. A surgical method comprising:
creating a first hole through a first vertebral body;
creating a second hole through a second vertebral body; and
inserting a distraction screw through the first hole and into the second hole, wherein the distraction screw is formed of at least one threaded portion and at least one non-threaded portion, wherein the distraction screw further comprises at least one deployable wing for contacting a lower surface of the first vertebral body.

14. The surgical method of claim 13, wherein the distraction screw is inserted at an oblique angle into the first hole and at an oblique angle into the second hole.

15. The surgical method of claim 13, wherein the distraction screw comprises a proximal end, a distal end and a connecting assembly therebetween.

16. The surgical method of claim 15, wherein the connecting assembly comprises a connecting portion, a swivel pin and a pin.

17. The surgical method of claim 16, wherein the swivel pin and pin are configured to couple.

18. The surgical method of claim 15, wherein the connecting assembly forms a swivel joint.

19. The surgical method of claim 13, wherein the distraction screw comprises a cannulated actuator.

20. The surgical method of claim 19, wherein the distraction screw further comprises at least two deployable wings.

* * * * *